United States Patent [19]

Phipps

[11] Patent Number: 5,403,275

[45] Date of Patent: * Apr. 4, 1995

[54] METHOD FOR REDUCING SENSATION IN IONTOPHORETIC DRUG DELIVERY

[75] Inventor: J. Bradley Phipps, Plymouth, Minn.

[73] Assignee: Alza Corporation, Palo Alto, Calif.

[ * ] Notice: The portion of the term of this patent subsequent to Jun. 22, 2010 has been disclaimed.

[21] Appl. No.: 80,341

[22] Filed: Jun. 21, 1993

Related U.S. Application Data

[63] Continuation of Ser. No. 679,425, Apr. 2, 1991, Pat. No. 5,221,254.

[51] Int. Cl.$^6$ .............................................. A61N 1/30
[52] U.S. Cl. ................................... 604/20; 128/898; 604/890.1; 607/3
[58] Field of Search ................... 604/20, 40; 128/898; 607/149, 151

[56] References Cited

U.S. PATENT DOCUMENTS

| | | |
|---|---|---|
| 3,989,816 | 11/1976 | Rajadhyaksha . |
| 3,991,755 | 11/1976 | Vernon et al. . |
| 4,141,359 | 2/1979 | Jacobsen et al. . |
| 4,211,222 | 7/1980 | Tapper . |
| 4,250,878 | 2/1981 | Jacobsen . |
| 4,340,047 | 6/1982 | Tapper . |
| 4,382,529 | 5/1983 | Webster . |
| 4,398,545 | 8/1983 | Wilson . |
| 4,405,616 | 9/1983 | Rajadkyaksha . |
| 4,406,658 | 9/1983 | Lattin et al. . |
| 4,415,563 | 11/1983 | Rajadkyaksha . |
| 4,424,210 | 1/1984 | Rajadhyaksha . |
| 4,744,787 | 5/1988 | Phipps et al. . |
| 4,747,819 | 5/1988 | Phipps et al. . |
| 4,752,285 | 6/1988 | Petelenz . |
| 5,167,616 | 12/1992 | Haak et al. ............................ 604/20 |
| 5,221,254 | 6/1993 | Phipps .................................. 604/20 |
| 5,246,418 | 9/1993 | Haynes et al. ........................ 604/20 |

FOREIGN PATENT DOCUMENTS

| | | |
|---|---|---|
| 0058920 | 9/1982 | European Pat. Off. .............. 604/20 |
| 0318776 | 6/1989 | European Pat. Off. .............. 604/20 |
| 0410009 | 5/1934 | United Kingdom .................. 604/20 |

OTHER PUBLICATIONS

H. Molitor "Experimental Studies on the Causes and Prevention of Iontophoretic Burns", 198 Am. J. Med. Sci. pp. 778–785 (1939).

J. B. Phipps, Abstract of Paper presented Aug. 1989, "The Effect of Extraneous Ions on the Transdermal Iontophoretic Delivery of Hydromorphine".

R. Burnett et al., "Characterization of the Permselective Properties of Excised Human Skin during Iontophoresis", *J. Pharm. Sciences*, pp. 765–776 (1987).

*Primary Examiner*—John D. Yasko
*Assistant Examiner*—Ceralin Smith
*Attorney, Agent, or Firm*—Grady J. Frenchick

[57] ABSTRACT

Methods for delivering therapeutic agents by iontophoresis with reduced or mitigated sensation are disclosed. The methods generally involve the step of delivering therapeutic agent by iontophoresis in the presence of an intentionally added sensation reducing amount of a multivalent ion. Preferred multivalent ions useful to mitigate sensation are calcium, magnesium, phosphate and zinc.

6 Claims, 2 Drawing Sheets

METHOD FOR REDUCING SENSATION IN IONTOPHORETIC DRUG DELIVERY

CROSS REFERENCE TO RELATED APPLICATION

This is a continuation application of application Ser. No. 07/679,425, filed Apr. 2, 1991, now U.S. Pat. No. 5,221,254, issued Jun. 22, 1993.

TECHNICAL FIELD

The present invention generally concerns methods for the electrically assisted administration or delivery of therapeutic agents or species. Yet more specifically, this invention relates to electrically assisted methods for delivering agents or drugs with reduction or elimination of skin sensation.

BACKGROUND OF THE INVENTION

The present invention concerns methods for transdermal delivery or transport of therapeutic agents, typically through iontophoresis. Herein the terms "iontophoresis" and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (i.e., 100% ionized), completely uncharged, or partly charged and partly uncharged. The therapeutic agent or species may be delivered by electromigration, electroosmosis or a combination of the two. Electroosmosis has also been referred to as electrohydrokinesis, electro-convection, and electrically-induced osmosis. In general, electroosmosis of a therapeutic species into a tissue results from the migration of solvent, in which the species is contained, as a result of the application of electromotive force to the therapeutic species reservoir.

As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be transdermally delivered. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, Vernon et al. U.S. Pat. No. 3,991,755; Jacobsen et al. U.S. Pat. No. 4,141,359; Wilson U.S. Pat. No. 4,398,545; and Jacobsen U.S. Pat. No. 4,250,878 disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is positively charged, then the positive electrode (the anode) will be the active electrode and the negative electrode (the cathode) will serve to complete the circuit. If the ionic substance to be delivered is negatively charged, then the cathodic electrode will be the active electrode and the anodic electrode will be the counter electrode.

Alternatively, both the anode and the cathode may be used to deliver drugs of opposite charge into the body. In such a case, both electrodes are considered to be active or donor electrodes. For example, the anodic electrode can drive positively charged ionic substances into the body while the cathodic electrode can drive negatively charged ionic substances into the body.

Furthermore, existing iontophoresis devices generally require a reservoir or source of the ionized or ionizable species (or a precursor of such species) which is to be iontophoretically delivered or introduced into the body. Examples of such reservoirs or sources of ionized or ionizable species include a pouch as described in the previously mentioned Jacobsen U.S. Pat. No. 4,250,878, a pre-formed gel body as disclosed in Webster U.S. Pat. No. 4,382,529 and a generally conical or domed molding of U.S. Pat. No. 4,722,726 to Sanderson et al. Such drug reservoirs are electrically connected to the anode or the cathode of an iontophoresis device to provide a fixed or renewable source of one or more desired species or agents.

Recently, the transdermal delivery of peptides and proteins, including genetically engineered proteins, by iontophoresis has received increasing attention. Generally speaking, peptides and proteins being considered for transdermal or transmucosal delivery have a molecular weight ranging between about 500 to 40,000 daltons. These high molecular weight substances are usually too large to diffuse passively (i.e., without electromotive force) through skin at therapeutically effective rates. Since many peptides and proteins carry either a net positive or net negative charge and because of their inability to diffuse passively through skin, they are considered likely candidates for iontophoretic delivery as defined herein.

One of the technical hurdles that, heretofore, has not been overcome has been the problem of the patient feeling the electrical current applied by the iontophoretic delivery device. In severe cases (e.g., at high current densities), the sensation can be painful. Particularly during the moments of drug delivery shortly after application of the iontophoretic drug delivery device to a patient's skin, complaints of pain, stinging, itching, tingling, prickliness, burning, or other unwanted or undesired skin sensation have been voiced. All of these various responses are to be considered forms of sensation within the contemplation of the present invention.

This technical hurdle has been addressed in the art. In an early article, H. Molitor et al. in "Experimental Studies on the Causes and Prevention of Iontophoretic Burns", 198 *Am. J. Med. Sci*, 778–785 (1939) reported on the occurrence of burns caused by pH changes, and that there was a definite relationship between pain and irritation and such pH changes in the skin.

U.S. Pat. No. 4,211,222 to Robert Tapper suggests that pain or tingling due to passage of current may be reduced by the use of a larger positive electrode. The method of the '222 Tapper patent employs a porous intervenor material between the electrode and the patient's skin. The intervenor has a thickness which is very large in relation to the thickness of the patient's skin between the electrode and the patient's skin.

U.S. Pat. No. 4,340,047 also to Robert Tapper discloses a self-treatment iontophoretic treatment apparatus. The '047 patent suggests the gradual imposition of a treatment period to reduce the possibility of electrical shock. A delay means is employed in the device of the '047 patent to impose the drug treatment current gradually when the device is activated by placing a load across its terminals.

U.S. Pat. No. 4,406,658 to Gary A. Lattin et al. discloses an iontophoretic device in which the polarity of the electrodes is reversible. As disclosed by Lattin et al. current is reduced prior to switching of polarities to avoid the possibly unpleasant sensation of having the polarities change while the device is operating at a therapeutic current level.

J. Bradley Phipps et al. in the abstract of their paper presented to the Controlled Release Society Meeting of August, 1989 describe the effect of "extraneous" ions, that is, ions having the same charge of the drug to be delivered, on the delivery of hydromorphone. The presence of extraneous ions may reduce the efficiency of drug delivery from an iontophoretic delivery device since the extraneous ions compete with the drug ions for carrying current into the body. Phipps et al. accordingly teach the desirability of minimizing the amount of extraneous ions available to compete with the species or agent to be delivered. Extraneous ions whose effect was described in the Phipps et al. paper include lithium, calcium, potassium, sodium and magnesium. Phipps et al. make no mention of stinging or other skin sensation(s), encountered in the delivery of the desired or extraneous ions.

None of the above references, alone or in combination, disclose or suggest the present invention.

BRIEF DESCRIPTION OF THE INVENTION

Briefly, in one aspect, the present invention is a method of reducing, minimizing or eliminating skin sensation of applied electrical current during iontophoretic drug delivery. The method involves the steps of selecting and intentionally adding or providing to the component of the electrotransport or iontophoresis device from which drug or agent is to be delivered, to the counter electrode, or to both, a multivalent ion other than the drug or agent which is to be delivered. The method involves the further step of delivering the selected drug or agent and the intentionally added multivalent ion through the patient's skin by electrically-assisted means, with discernable mitigation or elimination of sensation. In a preferred practice of this invention, the multivalent ion is positive and divalent and the mode of electrotransport or electrical assist is iontophoresis. In yet a more preferred practice of this invention, the multivalent ion is selected from the group consisting of calcium, zinc, phosphate, or magnesium.

In another practice, the present invention is utilized to reduce sensation during the first few seconds, to several minutes, after the start of electrically-assisted administration of a therapeutic agent to a patient (and multivalent ion). During this initial time period a therapeutic level or concentration of iontophoretically delivered species is established in the patient's blood stream. To shorten the time needed to establish a therapeutic blood concentration of delivered species in the patient, it may be desirable to operate an iontophoretic device at a higher current density during the time period immediately after its application of the device to a patient. This initial higher current density phase or time period is sometimes referred to as the "bolus period" or "bolus phase". The current density during the first or earlier bolus period is generally higher than the second or later, lower current density phase, when blood concentration of delivered species is held near a therapeutic or maintenance level. It is also during the bolus period when the patient is likely to be most sensitive to current-induced sensation because the patient, generally speaking, has not been acclimated, accommodated, or accustomed to the sensation of iontophoretic drug delivery. Thus, while the continued practice of this invention after the bolus period is contemplated, that is by the continued delivery of the intentionally added multivalent ion or ions during the maintenance phase, it is sensation reduction during the bolus period for which the advantage of this invention is most dramatic.

BRIEF DESCRIPTION OF THE FIGURES

A better understanding of the present invention as well as its objects and advantages will become apparent upon consideration of the following detailed description of the invention, especially when taken with the accompanying figures, wherein like numerals designate like parts throughout and wherein.

DETAILED DESCRIPTION OF THE INVENTION

Figure 1:
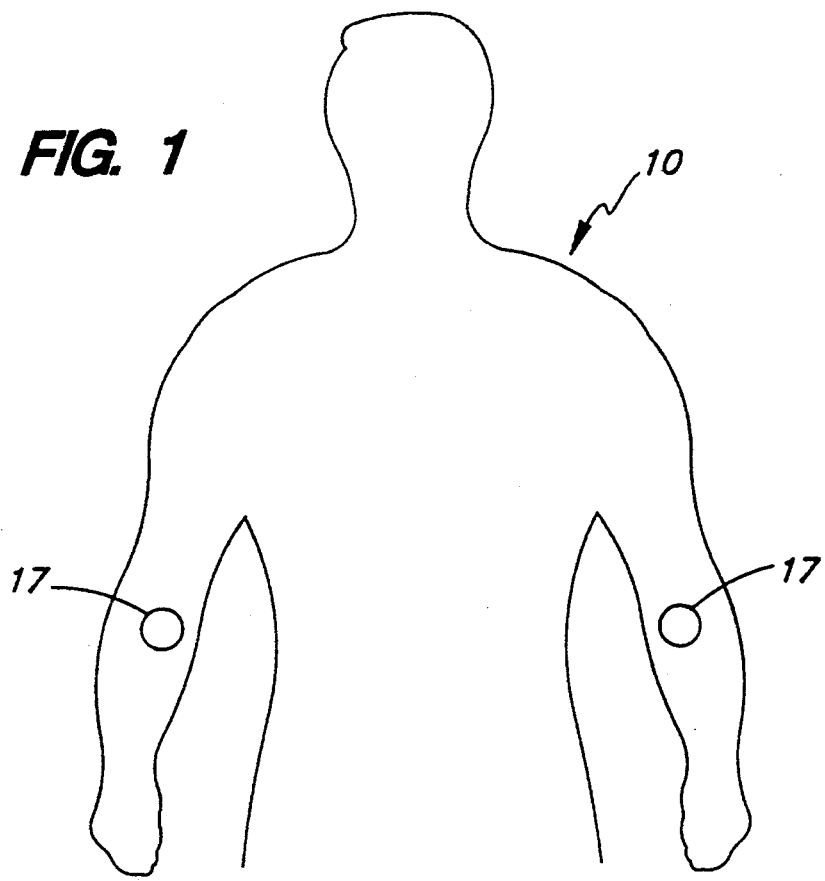
FIG. 1 is a schematic view of a patient with gel patch test devices attached to his forearms for sensation comparison purposes as described in the examples.

Thus there is shown in FIG. 1, a schematic depiction of a test subject 10 showing the forearm location of gel patch iontophoretic delivery devices 17. Return or counter electrodes (not shown) also would be attached to the patient's body to complete the electronic circuit when patches 17 are activated. The test protocol employed is more completely described below.

Figure 2:
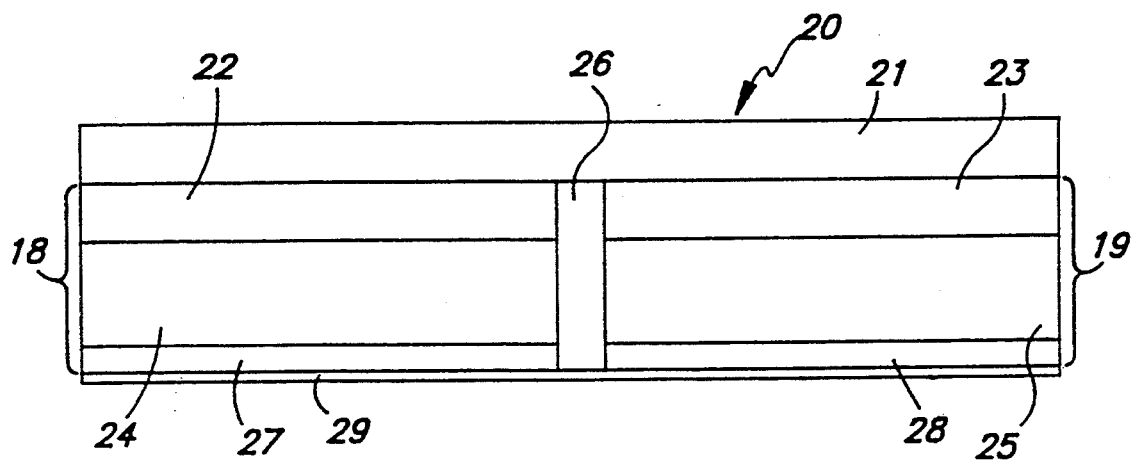
FIG. 2 is a schematic view of an iontophoretic delivery device useable in the method of this invention.

FIG. 2 is a schematic depiction of an iontophoretic delivery device 20 useable in the present invention. Device 20 has a top layer 21 which contains an electrical power supply (e.g., a battery or a series of batteries) as well as optional control circuitry such as a current controller (e.g., a resistor or a transistor-based current control circuit), an on/off switch, and/or a microprocessor adapted to control the current output of the power source over time. The details of this electronic circuitry and power source are conventional and are omitted so as not to unnecessarily complicate this description of the invention.

Device 20 comprises electrode assemblies indicated by brackets 18 and 19. Electrodes assemblies 18 and 19 are separated from one another by an electrical insulator 26, and form therewith a single self-contained unit. For purposes of illustration, the electrode assembly 18 will be referred to as the "donor" electrode assembly while electrode assembly 19 will be referred to as the "counter" electrode assembly. These designations of the electrode assemblies are not critical and may be reversed in any particular device or in operation of the device shown.

In the embodiment of FIG. 2, the donor electrode 22 is positioned adjacent drug reservoir 24 while the counter electrode 23 is positioned adjacent the return reservoir 25 which contains an electrolyte. Electrodes 22 and 23 may be formed from metal foils, or a polymer matrix loaded with metal powder, powdered graphite, carbon fibers, or any other suitable electrically conductive material. Reservoirs 24 and 25 can be polymeric matrices or gel matrices. Natural or synthetic polymer matrices may be employed. Insulator 26 is composed of a non-electrical conducting and non-ion-conducting material which acts as a barrier to prevent short-circuiting of the device 20. Insulator 26 can be an air gap, a non-ion-conducting polymer or adhesive or other suitable barrier to ion flow. The device 20 optionally can be adhered to the skin by means of ion-conducting adhesive layers 27 and 28. The device 20 also includes a strippable release liner 29 which is removed just prior to application of the device to the skin. Alternatively, device 20 can be adhered to the skin by means of an adhesive overlay of the type which are conventionally used in transdermal drug delivery devices. Generally speaking, an adhesive overlay would contact the skin around the perimeter of the device to maintain contact between reservoirs 24 and 25 and the patient's skin.

In a typical device 20, the drug reservoir 24 contains a neutral, ionized, or ionizable supply of the drug or agent to be delivered and the counter reservoir 25 contains a suitable electrolyte such as, for example, sodium chloride, potassium chloride, or mixtures thereof. Either or both of the drug reservoir and counter reservoir may contain, alone or in a mixture with other species, multivalent ions as contemplated in this invention. Alternatively, device 20 can contain an ionizable, or neutral supply of drug in both reservoirs 24 and 25 and in that manner both electrode assemblies 18 and 19 would function as donor electrode assemblies. For example, positive drug ions could be delivered through the skin from the anode electrode assembly, while negative drug ions could be introduced from the cathode electrode assembly. Generally, the combined skin-contacting area of electrode assemblies 18 and 19 can range from about 1 cm$^2$ to about 200 cm$^2$, but typically will range from about 5 cm$^2$ to about 50 cm$^2$.

In accordance with the present invention, the drug reservoir 24 and return reservoir 25 of the iontophoretic delivery device 20 must be placed in agent or drug transmitting relation with the patient so as to iontophoretically deliver agent or drug. Usually this means the device is placed in intimate contact with the patient's skin. Various sites on the human body may be selected depending upon the physician's or the patient's preference, the drug or agent delivery regimen or other factors such as cosmetic.

In accordance with one practice of the invention, a multivalent, preferably divalent, ion is intentionally added to drug reservoir 24. Device 20 then is applied to the patient's skin (after removal of liner 29) and activated. Activation of device 20 causes agent and multivalent ion to be iontophoretically delivered with a perceptible (from the patient's viewpoint) reduction in sensation as compared to delivery of just agent.

In a preferred practice, a positive, divalent ion, such as calcium ion, magnesium ion, or zinc ion (or a precursor or ion-generating neutral species such as a salt) is added. These preferred species, particularly in small amounts, have been found to reduce skin sensation of the applied current at the drug or agent delivery site. Calcium ion in particular has been found to reduce sensation, even if other ions, such as sodium ions which have been discovered to enhance the patient's sensation, are present.

In accordance with another practice of this invention, a multivalent, preferably divalent, ion is intentionally added to the return reservoir 25. For example, if the therapeutic agent to be delivered is anionic, then the cation content of the return reservoir would be entirely or partly multivalent ion. The multivalent ion of choice for this purpose is calcium. If the therapeutic agent to be delivered is cationic, then the anionic content of the return reservoir would be entirely or partly multivalent. The multivalent ion of choice for this purpose would be phosphate (i.e., NaPO$_4^{2-}$, or PO$_4^{3-}$).

It is very surprising and unexpected that the addition of a multivalent ion would reduce sensation. None of the prior art references or patents mentioned above describe or in any way disclose or suggest that the addition of a multivalent ion to the drug reservoir or return reservoir and thus to the delivery process, especially in limited amounts, reduces sensation. In fact, the art, generally speaking, teaches away from the addition of non-drug or "extraneous" ions to the drug reservoir of the device. The reason for this teaching is very simple. The greater the number of non-drug ions capable of responding to generated electrical fields, the lower the overall drug delivery efficiency of the device. In other words, the intentional addition and delivery of multivalent ions having the same ionic charge as the drug ions, as described herein, reduces the amount of drug delivered per unit of electrical current. The non-drug multivalent ions carry a portion of the electrical current between the device and the patient which might otherwise be carried by drug agent or drug species. However, in order to achieve the advantage of reduced sensation during electrically-assisted, transdermal drug delivery, some reduction in overall device drug delivery efficiency can be tolerated, particularly during the bolus period.

When delivering drugs transdermally by iontophoresis from a device having a current density greater than about 0.1 mA/cm$^2$ and, in particular, greater than about 0.5 mA/cm$^2$, the patient feels the electric current applied by the device for the about first hour of operation of the device. Generally speaking, thereafter the patient's ability to feel the applied current decreases. It has also been determined that the addition of extraneous multivalent ions beyond a certain content in the drug reservoir produces no significant additional sensation reducing effect. These two observed phenomena can be used to optimize the amount of extraneous multivalent ions loaded in the drug reservoir of the iontophoretic delivery device.

In order to optimize the amount of multivalent ion present in the drug reservoir, it is most advantageous to add an amount of multivalent ion which will be completely delivered during about the initial hour (preferably about 1 to 20 minutes) after the start of delivery of agent or species. Such an amount reduces the patient's ability to feel the electrical current during the critical "bolus" period. It also has minimal adverse effect on overall device drug delivery efficiency because there are fewer non-drug ions present to reduce delivery efficiency during the phase after "bolus" period. In this manner, the drug delivery efficiency of the device is only compromised during the initial "bolus" period, during which period the treatment of patient sensation is most critical.

In general, the amount of multivalent ion added to the reservoir can be determined on an experimental basis by those skilled in the art. The amount of multivalent ion needed to reduce sensation will vary depending upon a number of factors including the current density applied by the device, the particular drug being delivered, the content of ions in the reservoir, the degree of sensation reduction desired, as well as the acceptability of lower drug delivery efficiency from the device. In general, those skilled in the art can experimentally determine suitable multivalent ion content for the drug reservoir or the return reservoir (or both) following the teachings contained herein and especially the attached examples.

The terms "agent" or "drug" are used extensively herein. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

It is believed that, the method of the present invention can be used to deliver, with reduced sensation, the following drugs: baclofen, betamethasone, beclomethasone, buspirone, cromolyn sodium, dobutamine, doxazosin, droperidol, fentanyl, sufentanil, ketoprofen, lidocaine, metoclopramide, methodtrexate, miconazole, midazolam, nicardipine, prazonsin, piroxicam, scopolamine, testosterone, verapamil, tetracaine, diltiazem, indomethacin, hydrocortisone, terbutaline and encainide.

This invention is also believed to be useful in the iontophoretic delivery, with reduced sensation, of peptides, polypeptides and other macromolecules typically having a molecular weight of at least about 300 daltons, and typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.,), follicle luteoids, αANF, growth factor releasing factor (GFRF), βMSH, somatostatin, bradykinin, somatotropin, platelet-derived growth factor, asparaginase, bleomycin sulfate, chymopapin, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin, antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

Generally speaking, it is most preferable to use a water soluble salt of the drug or agent to be delivered. Drug or agent precursors, i.e., species which generate the selected species by physical or chemical processes such as ionization, dissociation, or dissolution, are within the definition of "agent" or "species" herein. "Drug" or "agent" is to be understood to include charged and uncharged species as described above.

In certain cases, it may be desirable to deliver the drug or agent with a one or more skin permeation enhancers. A skin permeation enhancer can be selected from any of a wide variety of known materials capable of enhancing transdermal drug flux. Known permeation enhancers include, for example, surfactants, alkyl substituted sulfoxides, alkyl polyethylene glycols, lower alcohols and the permeation enhancers disclosed in U.S. Pat. Nos. 3,989,816; 4,405,616; 4,415,563; 4,424,210; and 4,722,726 all of which are incorporated herein by reference. Having thus generally described the invention, the following examples will further illustrate selected preferred embodiments.

EXAMPLES

A. Electrode Preparation

Agar gel discs were prepared having a 2.5 cm diameter and a thickness of 0.3 cm. The gel discs were soaked in distilled water for three days to remove substantially all extraneous ions. After soaking in distilled water, the gel discs were placed in a one molar electrolyte solution (approximately 40 gel discs/liter) and soaked for at least three days to absorb the ionic electrolyte species. The following aqueous electrolyte solutions were used: sodium phosphate, sodium citrate, sodium acetate, sodium sulfate, magnesium chloride, lithium chloride, zinc chloride, calcium chloride, potassium chloride and sodium chloride.

Figure 3:
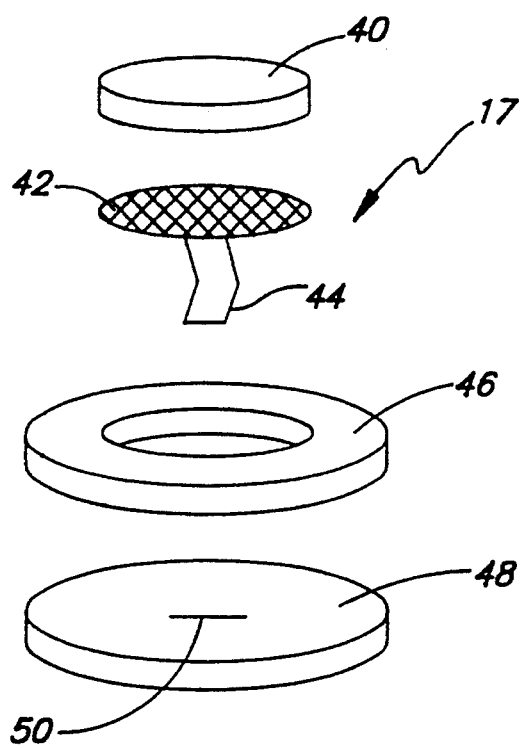
FIG. 3 is an exploded view of a gel patch as described in the examples.

Gel patches were prepared having the construction shown in FIG. 3. Gel patch 17 comprises a gel insert 40 prepared as described herein, a wire mesh, or current distribution member 42 having a silver tab 44 welded thereto, a medical grade polyethylene foam ring 46, and a medical grade polyethylene foam backing 48 with a slot 50, therein. Members used as anodes were composed of silver while those used as cathodes were composed of partially chloridized silver. When assembled, silver tab 44 slides through slot 50 to provide a connection to external electronics.

The agar gel disks were removed from the solutions one day prior to testing and glued into the electrode housings using a small amount of hot agar.

B. Experimental Set Up

Figure 4:
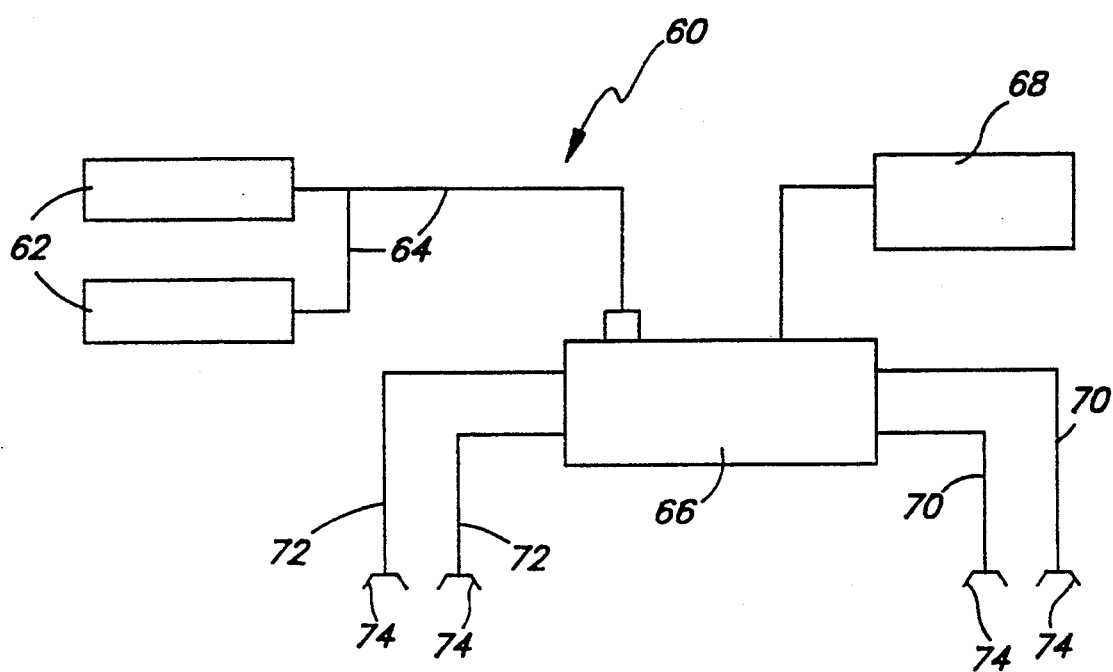
FIG. 4 is a circuit diagram of the device used for comparison testing of the gel patches shown in FIG. 3.

FIG. 4 is a circuit diagram 60 for an apparatus used to test gel patches 17. Circuit 60 comprises 12 volt batteries 62 coupled via leads 64 to a current source 66 which is, in turn, coupled to a multi-meter 68 used to monitor the voltage and also adjust the initial current setting. Current source 66 is connected to right and left leads 70 and 72, respectively. One of each of the right and left leads is connected (e.g., by aligator clips 74) to patch 17, the remaining of each left and right lead being placed, by means of a conductive adhesive, on the subject's back. In this manner, the electrical circuit to the gel patches to be tested was completed. Prior to applying the current, each arm was washed with distilled water and dried. The electrodes were placed on equivalent sites of each forearm, avoiding visible defects in the skin such as cuts, bites, scratches, etc. The leads were then attached to each electrode.

C. Experimental Design

In brief, the sensation caused by a particular ion was systematically compared to that caused by each of several other ions by placing one patch on the left arm and one patch on the right arm of a subject and applying current. The subject was then asked to compare the sensation caused by one ion on one arm to that caused by the other ion on the other arm using the following scale:

no difference=0
slightly more=1
moderately more=2
considerably more=3

All studies were performed in a double blind fashion to eliminate both subject and evaluator bias.

In a large study, patches containing 8 different ions (sodium, potassium, acetate, calcium, chloride, phosphate, sulfate, citrate) were applied to 8 subjects. Fifteen ion pairs, that is, 15 patches on the left arm and 15 patches on the right arm were administered to the subjects. Each subject, was tested with 6 of the 8 ions. The 15 pairs were applied, one pair at a time, in 3 testing sessions using 5 different patch sites on each forearm. At least 24 hours was allowed between testing sessions. No subject had the same set of ions administered to him or her. The overall consequence of this study design was that all ion combinations (e.g., sodium compared to calcium, acetate compared to potassium, etc.) were tested 4 times, twice left-right and twice right-left, on four different subjects.

D. Data Collection

The current was first adjusted to 0.5 mA (0.1 mA/cm$^2$) ($\pm 2\%$). After 5 seconds the current was raised to 1 mA (0.2 mA/cm$^2$) and the subject alerted to start concentrating on the difference in sensation caused by the two patches. After 30 seconds the subject was asked to identify in which arm he or she felt more sensation and their response was recorded. The subject was then asked to rate the difference in sensation according to the scale described above.

The current was then gradually (i.e., over a 5 second period) raised in 0.5 mA increments. At each current level, the subject was, after 30 seconds, asked to rate differences, if any, in sensation. The maximum current applied was 3 mA (0.6 mA/cm$^2$). The current was turned off after the 3 mA test and questions concerning the type of sensation were asked. The next pair of arm electrodes were placed on new forearm sites and the entire sequence repeated until all pairs of arm patches had been tested.

Smaller Studies

A number of smaller studies comparing fewer than the original 8 ions were run. In these smaller studies, the compositions chosen for testing reflected various hypothesis about the factors involved in producing sensation. In two smaller studies, the effects of magnesium, zinc and lithium ion on sensation were evaluated.

From earlier work it was known that there was a relationship between current level and sensation experienced—the higher the current, the higher the sensation rating. Also, at above 3 mA (0.6 mA/cm$^2$) the sensation experienced for some ions became quite painful. On the other hand, below about 0.5 mA (0.1 mA/cm$^2$) the sensations produced by some ions were so slight that ions could not be reliably differentiated.

Discussion of Results

The results of the first 8 ion study indicated that iontophoretic delivery of these ions under indentical test conditions produced varying magnitudes of the sensation during DC stimulation. Sodium ion was found to produce the greatest level of sensation while calcium ion was found to produce the lowest level of sensation. At a current density of 200 μA/cm$^2$, the sensation-causing ranking, from least to most, was found to be:

calcium, phosphate<chloride<acetate<citrate, sulfate<potassium<sodium.

At a current density of 600 μA/cm$^2$, the ranking was:
calcium<phosphate<acetate<sulfate, citrate, chloride potassium, sodium.

As can be seen from the above rankings, multivalent ions, in general, caused less sensation than monovalent ions. In particular, divalent calcium caused much less sensation than the monovalent cations sodium and potassium.

Two other studies were run to compare sensation caused by monovalent ions with sensation caused by divalent ions. In one study, the divalent cations $Zn^{2+}$ and $Ca^{2+}$ were compared to the monovalent ions $Na^{+1}$ and $Li^{+1}$. The results of this study clearly indicated that zinc and calcium caused less sensation than sodium and lithium.

In another four cation sensation study, the divalent ions $Ca^{2+}$ and $Mg^{2+}$ were compared to the monovalent ions $Na^+$ and $K^+$. Electrodes were prepared and tested as described above. Current levels of 0.5 mA, 1.0 mA, 2.0 mA, 3.0 mA and 4.0 mA were employed. The results of this study indicated that, in terms of increasing intensity of pain relative to each other, $Ca<Mg<<K<Na$ for currents less than 2.0 mA (0.4 $mA/cm^2$) with sodium and potassium ions being reversed for currents greater than 3.0 mA (0.6 $mA/cm^2$). Calcium ion was found to exhibit the least sensation, i.e., induced the least pain intensity, at all current levels, with magnesium ion only slightly more sensation-inducing. Potassium and sodium ion caused moderately to considerably more sensation than did calcium and magnesium.

A calcium-sodium sub-study was then conducted on mixtures of these two ions to see if a small amount of calcium (e.g., 10% Ca on a molar basis) would negate the effects of the more sensation-causing model drug ion, i.e., sodium ion. Four gel compositions were employed in this sub-study: 100% Ca, 90% Ca and 10% Na, 10% Ca and 90% Na, and 100% Na (all as chloride salts). The sensation caused by these formulations were systematically compared by each of four subjects using the methodology previously described. It was found that the 90 percent sodium with 10 percent calcium mixture gave ratings similar to that of the 100% calcium solutions. Thus, only a small quantity of calcium, e.g., 10 percent or less, is required to reduce sensation despite the presence of a much larger quantity of sensation-causing model drug ion (i.e., Na).

In general, using the data gathered from all studies, the ion ranking from least sensation to greatest sensation, was found to be:

calcium<phosphate, magnesium, zinc<chloride, acetate, citrate, sulfate<lithium, potassium, sodium.

These results were substantially the same at all current levels tested. Moreover, rankings at 30 seconds and 60 seconds were found to be substantially the same.

The results of the above studies suggest that when selecting an electrolyte for the return reservoir, one should select salts comprising multivalent ions. When the return reservoir is in contact with the cathode, then a preferred electrolyte would comprise a divalent cation, preferably calcium. Also inherent in the results of our studies, is the realization that one should avoid the use of monovalent ions, particularly monovalent cations such as potassium, sodium, and lithium. When the use of a sensation-causing ion is unavoidable (e.g. use of a therapeutic agent), then the addition of a small amount of a multivalent ion may considerably reduce the amount of sensation experienced by the patient as was shown by adding 10% calcium ions to the sodium model drug ions.

The above disclosure will suggest many alterations and variations to one of ordinary skill in the art. This disclosure is intended to be illustrative and not exhaustive. All such variations and permutations suggested by the above disclosure are to be included within the scope of the attached claims.

What is claimed is:

1. A method of reducing sensation of electrical current in operation of an iontophoretic drug delivery device comprising the steps of:
    a. providing an iontophoresis drug delivery device comprising a power source, an electrode assembly electrically coupled to the power source having a reservoir containing an agent to be iontophoretically delivered;
    b. intentionally adding an amount of physiologically acceptable multivalent ion to the apparatus reservoir sufficient to reduce sensation during drug delivery;
    c. placing the apparatus in contact with tissue; and
    d. operating the device to co-deliver a drug and said multivalent ion.

2. A method according to claim 1 wherein the multivalent ion is divalent.

3. A method according to claim 1 wherein the multivalent ion is positive.

4. A method according to claim 1 wherein the multivalent ion is divalent and positive.

5. A method according to claim 1 wherein the multivalent ion is selected from the group consisting of calcium, zinc, magnesium, and phosphate.

6. A method according to claim 1 wherein the multivalent ion is calcium and is present at a concentration of about 10 mole percent.

* * * * *